United States Patent
Azzolina

(10) Patent No.: US 10,722,628 B2
(45) Date of Patent: Jul. 28, 2020

(54) DEVICE FOR CARDIOCIRCULATORY ASSISTANCE

(71) Applicant: ELLEBI Fin LLC, Wilmington, DE (US)

(72) Inventor: Gaetano Azzolina, Licciana Nardi (IT)

(73) Assignee: ELLEBI Fin LLC, Wilmington, DE (US)

( * ) Notice: Subject to any disclaimer, the term of this patent is extended or adjusted under 35 U.S.C. 154(b) by 198 days.

(21) Appl. No.: 15/801,498

(22) Filed: Nov. 2, 2017

(65) Prior Publication Data

US 2018/0117225 A1 May 3, 2018

(30) Foreign Application Priority Data

Nov. 2, 2016 (IT) .............. 1020160110164

(51) Int. Cl.
*A61M 1/10* (2006.01)
*F04B 43/06* (2006.01)
*A61M 1/12* (2006.01)

(52) U.S. Cl.
CPC .......... *A61M 1/106* (2013.01); *A61M 1/1062* (2014.02); *A61M 1/1096* (2014.02); *A61M 1/122* (2014.02); *F04B 43/06* (2013.01); *A61M 1/127* (2013.01)

(58) Field of Classification Search
CPC ... A61M 1/1062; A61M 1/1096; A61M 1/122
See application file for complete search history.

(56) References Cited

U.S. PATENT DOCUMENTS 3,766,567 A * 10/1973 Kahn .................. A61M 1/1096
                                                     623/3.21
4,222,127 A    9/1980 Donachy et al.

FOREIGN PATENT DOCUMENTS

| EP | 1745809 A1 | 1/2007 |
| EP | 2101840 A1 | 9/2009 |
| EP | 2517739 A2 | 10/2012 |

* cited by examiner

*Primary Examiner* — Alyssa M Alter
(74) *Attorney, Agent, or Firm* — St. Onge Steward Johnston & Reens, LLC

(57) ABSTRACT

A device for cardiocirculatory assistance constituting a pump for a blood flow includes a body, a pair of covers, and a pair of membranes. The device is provided with a circuit for the passage of a gas or gaseous fluid alternatively under pressure and depressurization so that a reciprocating pumping motion of the membranes is established.

21 Claims, 8 Drawing Sheets

DEVICE FOR CARDIOCIRCULATORY ASSISTANCE

TECHNICAL FIELD

The present invention relates to a device for cardiocirculatory assistance, that is to say, to a haematic pump to be associated with the heart or to be used as its replacement.

PRIOR ART

The devices for cardiocirculatory assistance are devices intended to mechanically pump the blood, producing haematic flows of the pulsatile or continuous type. Such devices are used to solve clinical cases of reversible acute heart failure, such as heart attack, myocarditis, post-cardiotomy, or they are used to support the circulatory function waiting for heart transplantation or even indefinitely in case of irreversible chronic situations or problems. There exist different devices for ventricular assistance, both left and right or biventricular.

In the field of the production of devices for cardiocirculatory assistance solutions are known in which some membranes separate different chambers of which a central chamber enclosed between the membranes and a body of the device constitutes the chamber of passage of the blood that is sucked and then pumped into circulation and of which two side chambers are used as chambers of intake and suction of a deformation fluid of the membranes which consequently perform the pumping action on the first chamber, putting the blood into circulation.

Patent Application EP 2 101 840 describes a cardiocirculatory aiding device, as a haematic pumping device intended to provide right, left or biventricular assistance, which is supplied by means of a gas or gaseous fluid that provides the pneumatic pumping energy. The cardiocirculatory aiding device comprises a device generating a change in the pressure of the gas or gaseous fluid intended to be placed outside the human body, a blood pumping device intended to be installed inside the human body, a tubular duct of transmission of the gas or gaseous fluid that passes from inside the human body to outside the human body. The blood pumping device is driven by the change in the pneumatic pressure in the tubular duct by means of two opposite expandable and retractable lungs that compress an elastically yielding central chamber body by pulses in order to cause the pumping of the blood through two openings for blood input and blood output respectively, which are provided with one-way valves.

Patent Application EP 1 745 809 describes a device for cardiocirculatory assistance, also named ventricular assist device, comprising a haematic pump in which a pump body has an inner space defined by a rigid structure and a pair of mobile membranes alternatively driven in opposite directions by alternatively positive pressure and negative pressure gas or gaseous fluid. The gas or gaseous fluid is supplied in two recesses surrounding the two membranes. The gas or gaseous fluid is supplied by means of an external pneumatic force generating unit.

Patent Application U.S. Pat. No. 3,766,567 describes an artificial heart assembly comprising a pair of ventricles, a pair of atria or inflow means, a pair of sinus or outflow means for pumped blood, and fluid pumps to drive the ventricles. In a modification, a single ventricle is used as a ventricular assist device. Each ventricle has a shell providing a ventricular cavity and at least one pumping chamber in the shell. The chamber has a flexible non-stretching wall and a rigid wall sealed to each other. The rigid wall has an aperture to permit entry of the pumping fluid into the chamber. A blood-compatible material covers all blood-exposed surfaces in the cavity.

Patent Application U.S. Pat. No. 4,222,127 describes a blood pump for implant or paracorporeal use having a rigid case with inlet and outlet valves defining a pumping cavity. An integral thin walled flexible sac is arranged in correspondence of the pumping cavity. A flexible diaphragm is arranged inside the cavity and said diaphragm has a shape corresponding to the shape of the adjacent side of the sac. The case includes a control ring projecting into the cavity between the diaphragm and sac. The diaphragm is moved between diastolic and systolic positions to pump blood through the valves. During pumping, the ring distributes flexing of the diaphragm over an increased area while also preventing the interior walls of the sac from contacting each other. The outlet port and the portion of the sac immediately surrounding the outlet port are less flexible than the remainder of the sac away from the port. The portion of the diaphragm overlying the outlet port is less flexible than the remainder of the diaphragm. The less flexible portions of the sac and diaphragm improve pressure pulse pumping so that the more flexible portion of the sac away from the outlet port is initially collapsed and the sac is progressively collapsed from that portion to the outlet port to minimize stasis in the pumping chamber.

The prior art solutions are generally characterised by the use of essentially floppy membranes that, when one proceeds to the phase of expulsion of the blood from the chamber, cause blood swirls inside the chamber itself. The presence of such swirls results in the onset of phenomena of convergence of different blood flows inside the chamber with the generation of turbulences and with the consequence that the risk of formation of clots increases in zones, although small, of slowdown of the blood flow or blood stagnation zones and further with the risk of phenomena of high danger of changes in haematic health.

Furthermore, many prior art solutions are difficult to be housed inside the chest, both due to size and weight reasons.

Other drawbacks that can be found in the prior art solutions are due to their internal geometries and to their pumping modes, which can cause, in relation to the blood, haemolysis or formation of clots, also in this case with the risk of phenomena of high danger of changes in haematic health.

SUMMARY OF THE INVENTION

The aim of the present invention is to provide a device for cardiocirculatory assistance with a naturally physiological pulsated flow like the heart function which is easy to be manufactured and provided with a simplified-structure and small-sized intracorporeal part in order to facilitate its implantation also, but not exclusively, for paediatric use.

A further aim of the invention is to provide a device for cardiocirculatory assistance with pulsated flow with an improved configuration that allows to reduce, until at most eliminating, the problems of possible blood stagnations inside the chamber of the device, further allowing a reduction in the cellular trauma to which the blood is subjected.

The aim is achieved by the characteristics of the main claim. The sub-claims represent advantageous solutions.

The solution according to the present invention, by the considerable creative contribution the effect of which constitutes an immediate and important technical progress, has various advantages.

The solution according to the present invention allows a greater compliance with the principle at the basis of the physiology of the pulsatile blood circulation.

The solution according to the present invention allows to realize a device for cardiocirculatory assistance having much lower production costs than the prior art solutions.

DESCRIPTION OF THE DRAWINGS

In the following a solution is described with reference to the enclosed drawings, which are to be considered as a non-exhaustive example of the present invention in which.

DESCRIPTION OF THE INVENTION

Figure 1:
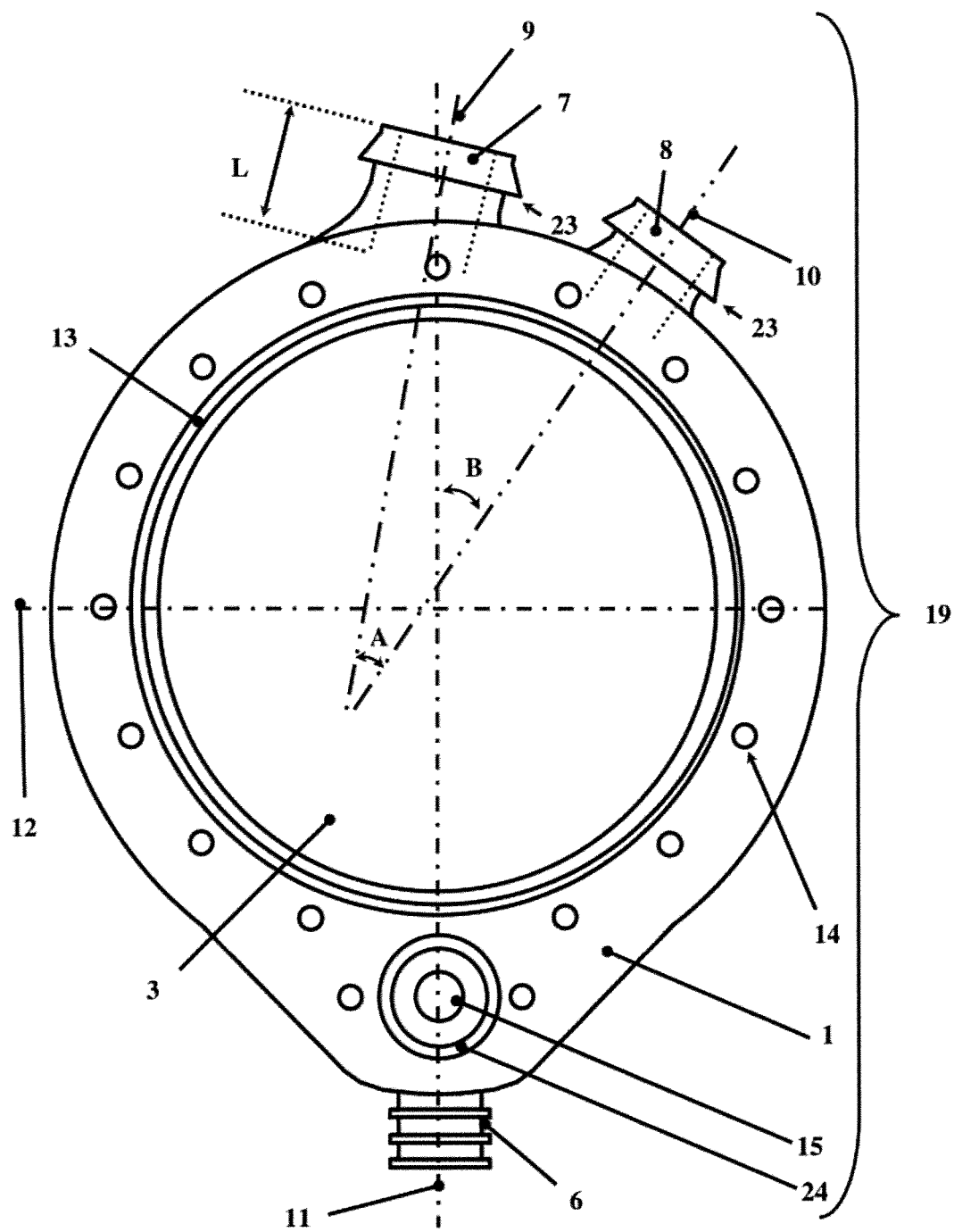
FIG. 1 is a front view of the body of the device for cardiocirculatory assistance made in accordance with the present invention.
Figure 2:
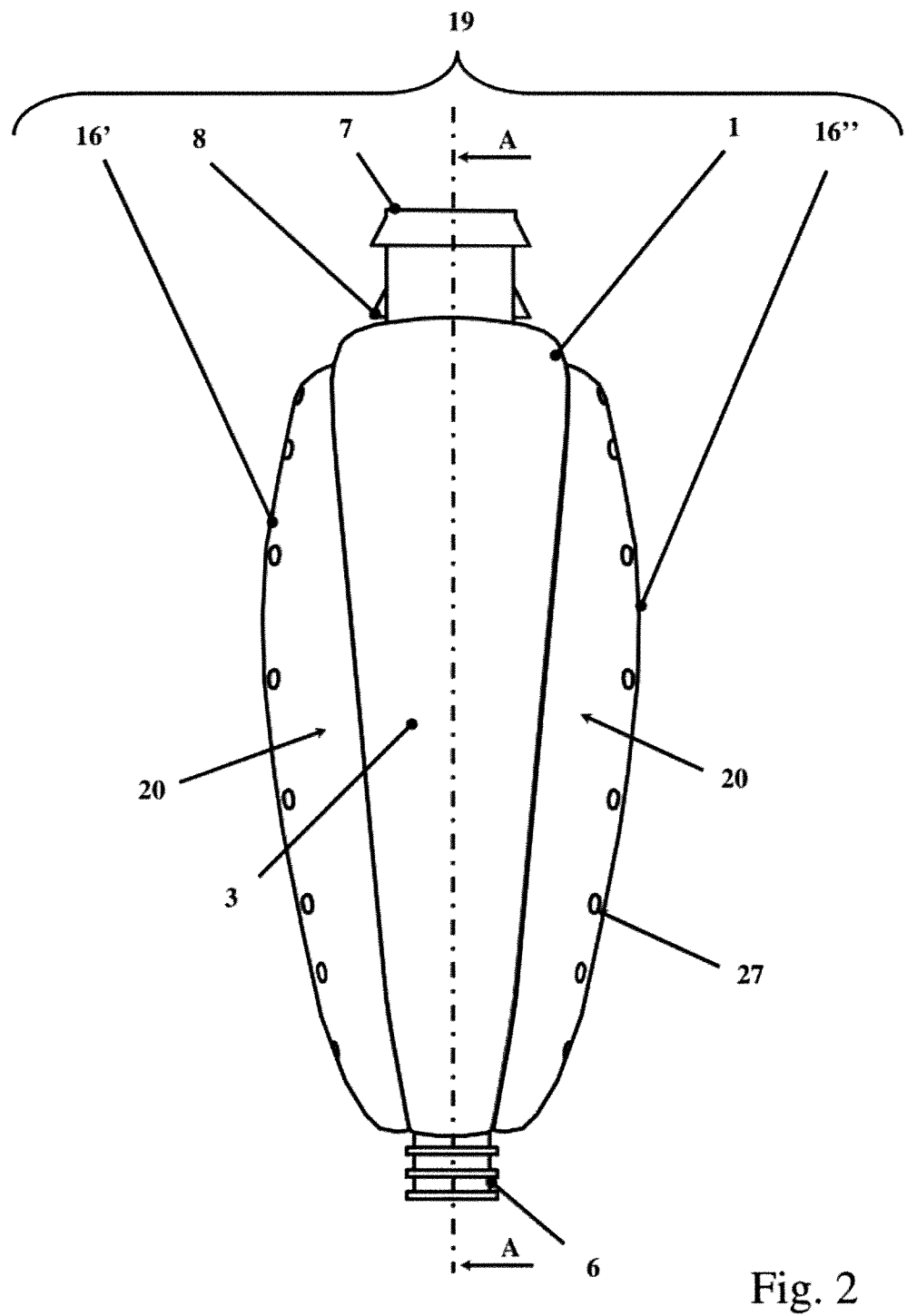
FIG. 2 is a side view of the device for cardiocirculatory assistance made in accordance with the present invention.
Figure 3:
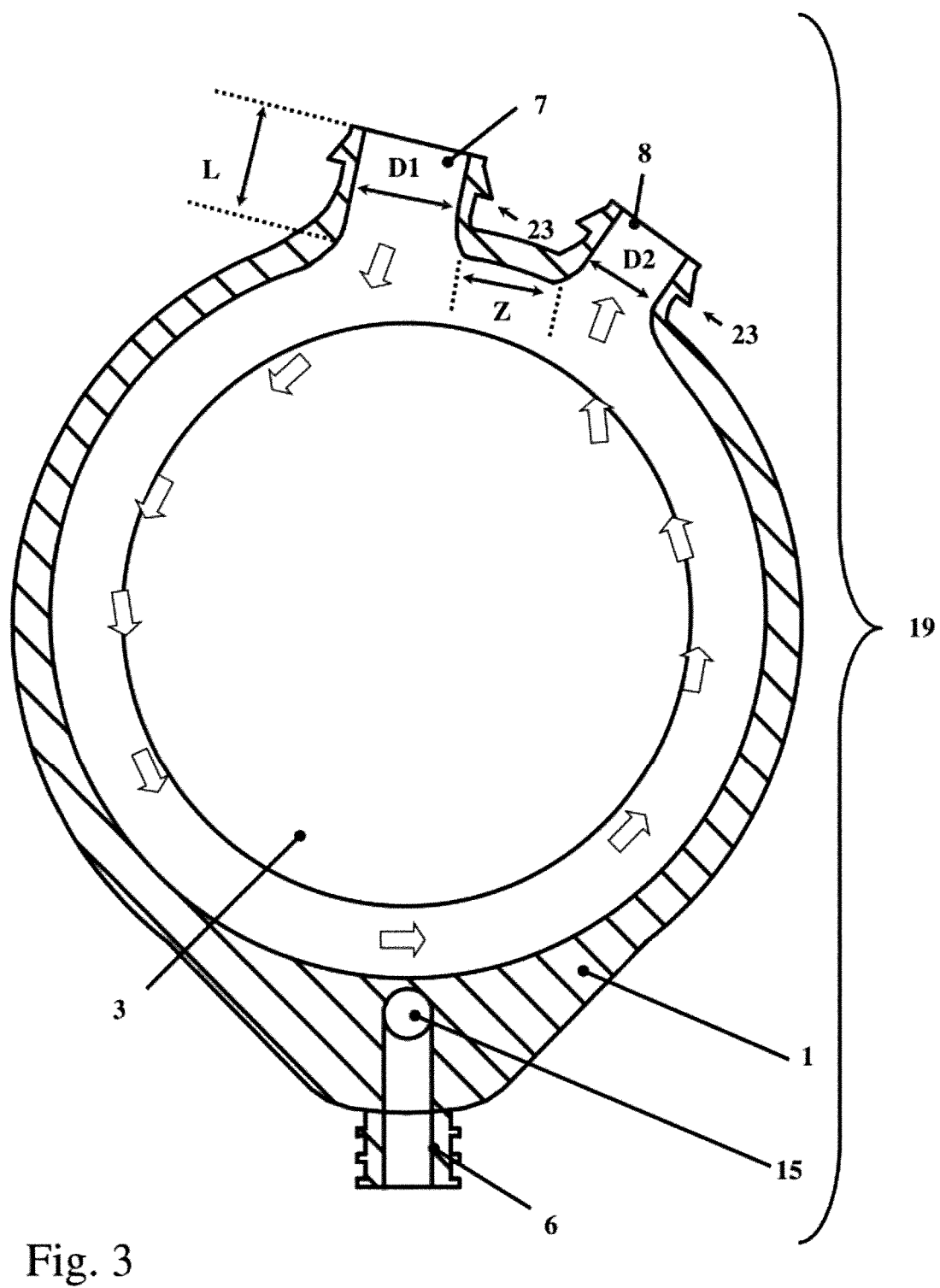
FIG. 3 is a sectional view of the device for cardiocirculatory assistance according to the section line indicated by A-A in FIG. 2.
Figure 4:
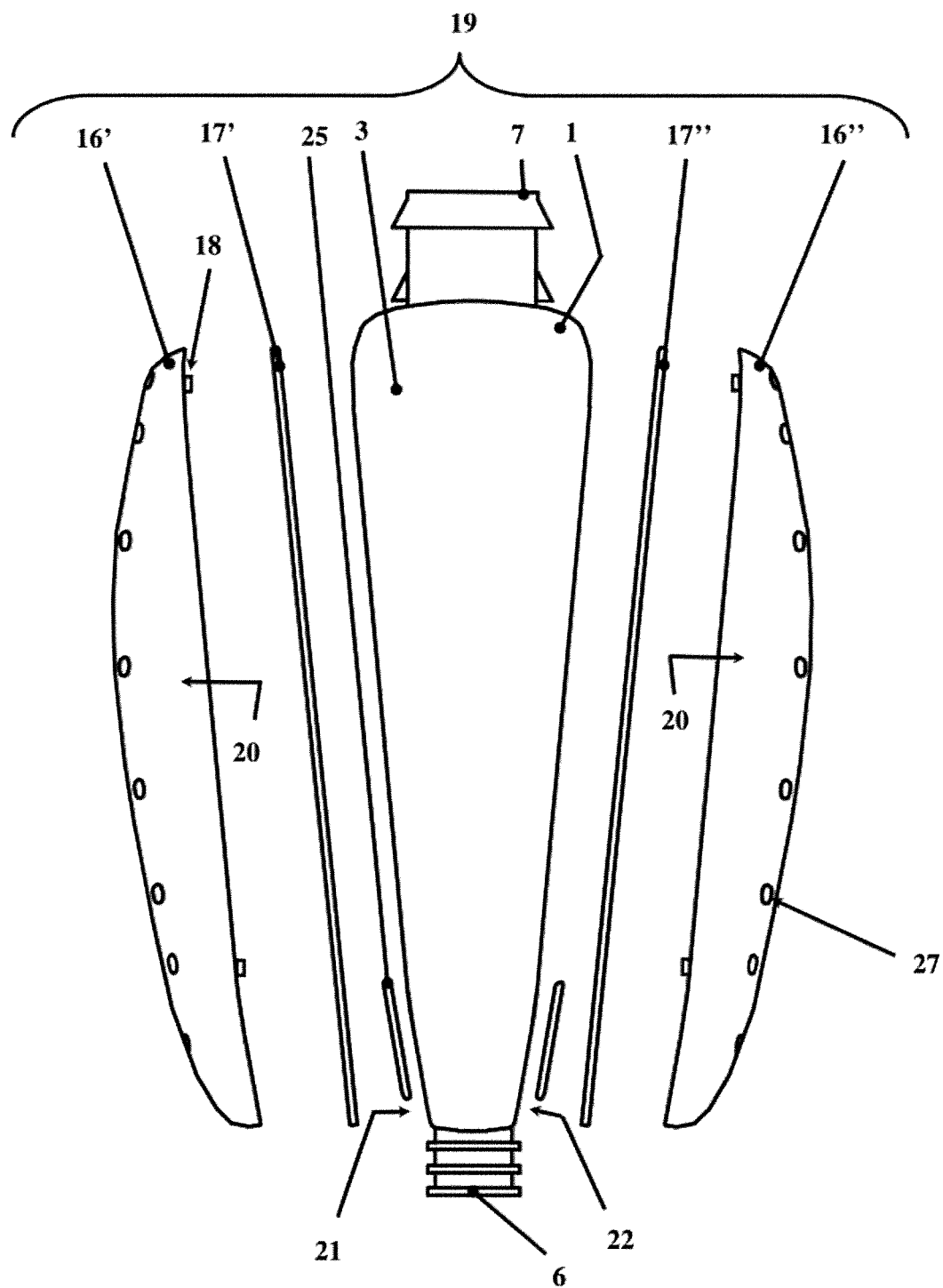
FIG. 4 is an exploded side view of the device for cardiocirculatory assistance made in accordance with the present invention.
Figure 5:
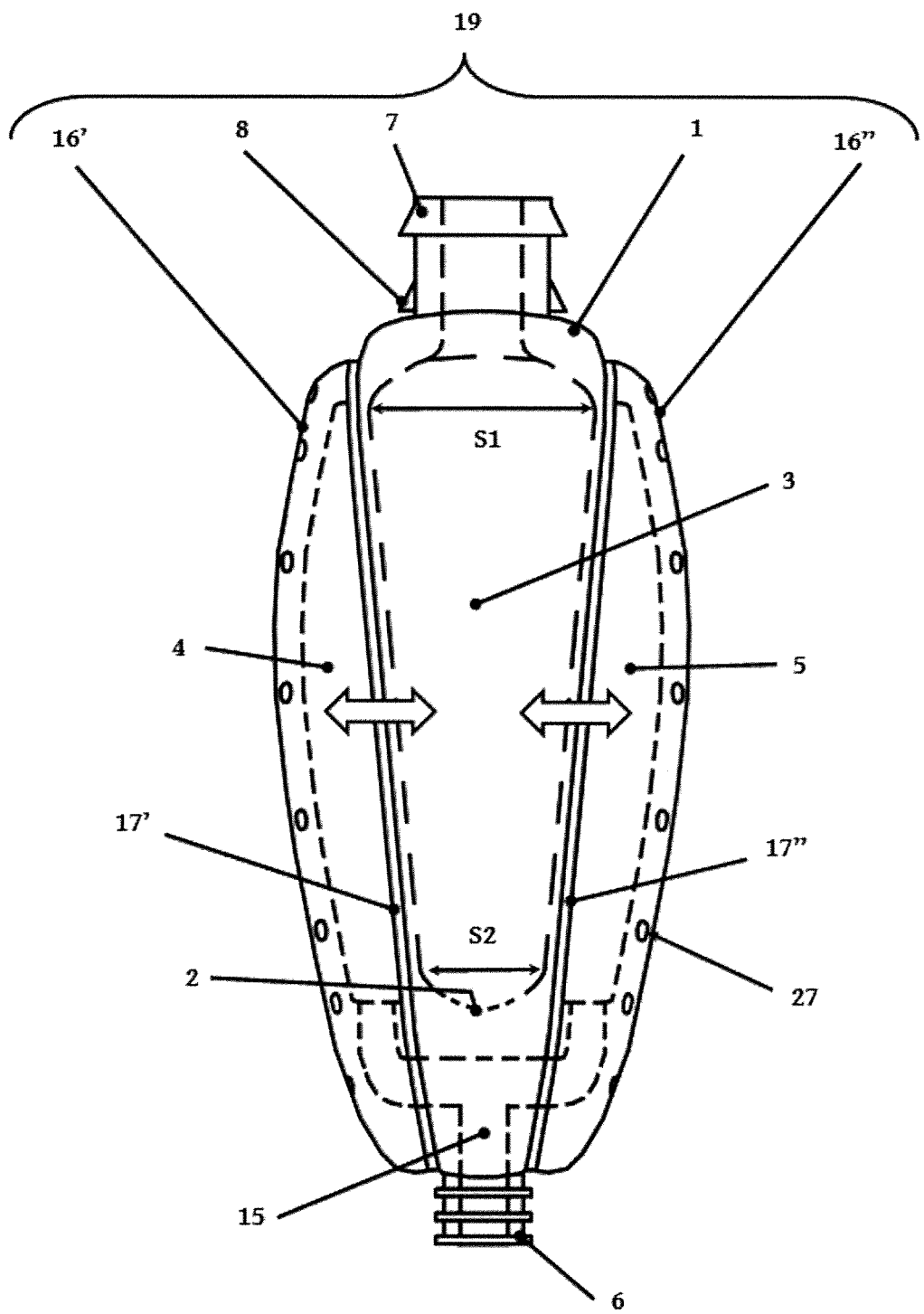
FIG. 5 is a side view of the device for cardiocirculatory assistance made in accordance with the present invention.
Figure 6:
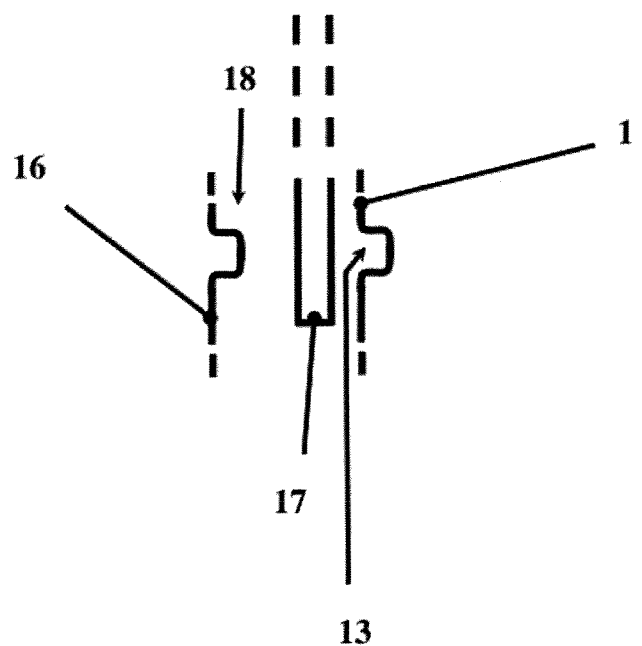
FIG. 6 is a detail showing the sealing of the membranes of the device for cardiocirculatory assistance made in accordance with the present invention.
Figure 7:
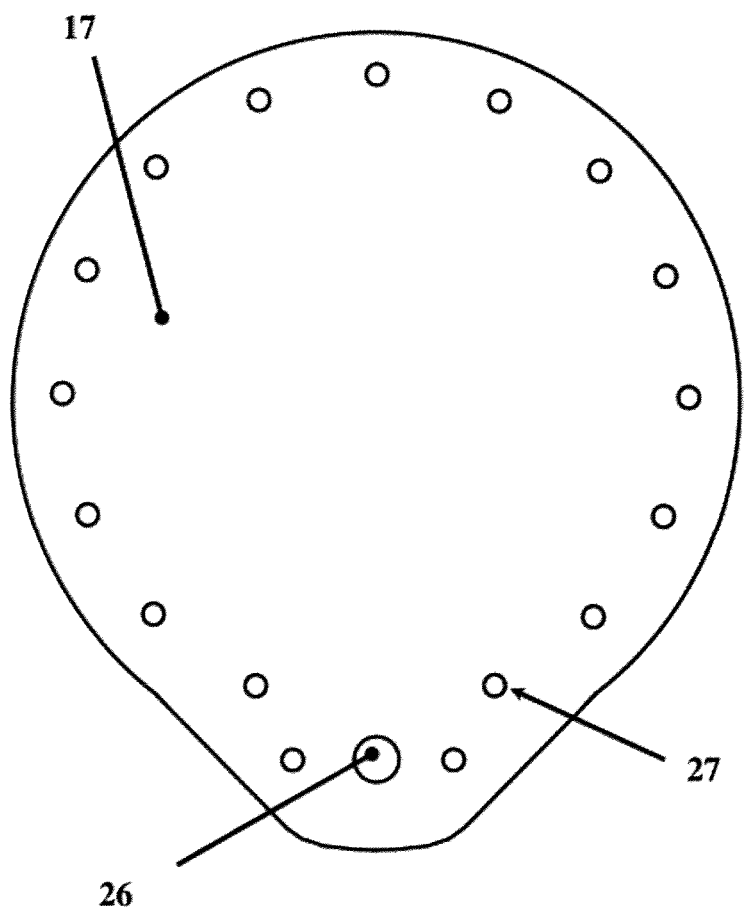
FIG. 7 is a front view of one of the membranes of the device for cardiocirculatory assistance made in accordance with the present invention.
Figure 8:
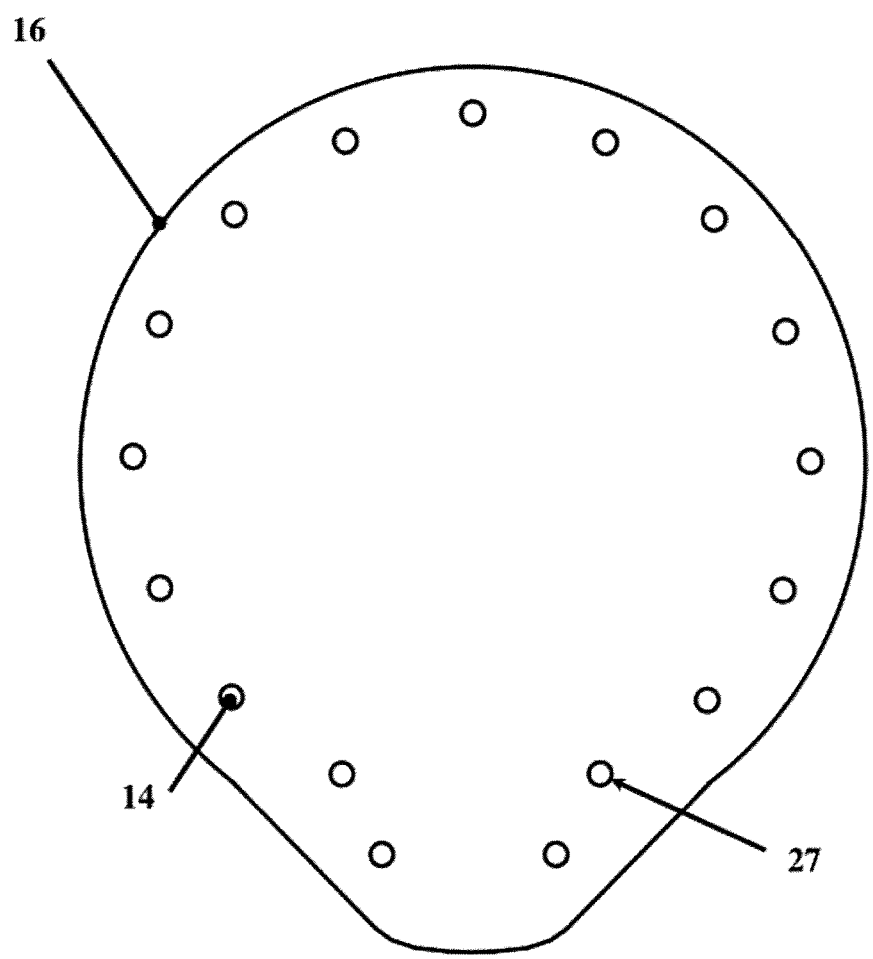
FIG. 8 is a front view of one of the covers of the device for cardiocirculatory assistance made in accordance with the present invention.

With reference to the figures (FIG. 1, FIG. 2, FIG. 3, FIG. 4, FIG. 5, FIG. 6, FIG. 7, FIG. 8), the device for cardiocirculatory assistance (19) made in accordance with the present invention comprises a body (1) provided with two opposite rigid shells in the form of covers (16, 16', 16") of which a first cover (16') and a second cover (16") enclose between them a clear space (3) of the body (1) in a sealed way.

The covers (16, 16', 16") are provided (FIG. 8) with through-holes (27) for the passage of fixing screws. The covers (16, 16', 16") are fixed to the body (1) preferably by means of a series of screws which are inserted into corresponding threaded holes (14) obtained on the body (1) perimetrically with respect to the clear space (3) of the body (1) to be sealed by means of the covers (16, 16', 16") themselves.

The covers (16, 16', 16") have an internally arched shape so as to define (FIG. 4) a cavity (20) that is coupled with the clear space (3) of the body (1).

Between each of the covers (16, 16', 16") and the body (1) there is positioned (FIG. 4, FIG. 5, FIG. 6) a respective membrane (17, 17', 17") in such a way as to seal the clear space (3) placed inside the body (1).

A first membrane (17') is placed between a first side (21) of the body (1) and the first cover (16') in such a way as to perimetrically seal the cavity (20) of the first cover (16') with respect to the clear space (3) of the body (1), thus constituting a first chamber (4).

A second membrane (17") is placed between a second side (22) of the body (1) and the second cover (16") in such a way as to perimetrically seal the cavity (20) of the second cover (16") with respect to the clear space (3) of the body (1), thus constituting a second chamber (5).

The membranes (17, 17', 17") are provided (FIG. 7) with through-holes (27) for the passage of fixing screws that are placed in such a way that, when the membrane is in the provided installation position, the through-holes (27) of the membrane (17, 17', 17") are aligned with the corresponding passing holes (27) of the cover (16, 16', 16") and with the threaded holes (14) obtained on the body (1).

Furthermore the membranes (17, 17', 17") are provided (FIG. 7) with an opening (26) for the passage of the pumping fluid, for example air or gas or gaseous fluid, the opening (26) being placed in such a way that, when the membrane is in the provided installation position, the opening (26) of the membrane (17, 17', 17") is aligned with a corresponding duct for the passage of the gas or gaseous fluid (15) of the body (1) which is in flow communication with the connection (6) for the pipe of connection to the pneumatic energy source that is used to supply the two opposite chambers (4, 5).

Furthermore, the opening (26) is placed in such a way that, when the membrane is in the provided installation position, the opening (26) of the membrane (17, 17', 17") is aligned with a corresponding duct for the passage of the gas or gaseous fluid of the cover (16, 16', 16") which is in flow communication with a respective chamber selected from the chambers (4, 5).

Around the outlet of the duct for the passage of the gas or gaseous fluid (15) of the body (1) there is (FIG. 1) a recess (24) for the insertion of a corresponding gasket (25) for sealing the duct for the passage of the gas or gaseous fluid that connects the connection (6) to the opposite chambers (4, 5), the duct extending with a "Y"- "V"- or "T"-shaped branching starting from the connection (6) up to the side wall of the body (1) then continuing through the respective covers (16, 16', 16").

Therefore, the device for cardiocirculatory assistance (19) is made (FIG. 4, FIG. 5) by means of the reciprocal fixing of the body (1), the first cover (16'), the first membrane (17'), the second cover (16"), the second membrane (17"). Since the first membrane (17') seals the first chamber (4) and the second membrane (17") seals the second chamber (5) according to a configuration in which the first membrane (17') and the second membrane (17") are facing each other in correspondence of the clear space (3), the clear space (3), too, is sealed by the membranes (17', 17") constituting by itself a third chamber, which is a discoid central chamber. Inside the sealed clear space (3) or third chamber the circulation of the blood takes place, the blood being introduced into the clear space (3) by means of a first port (7) or intake port and being expelled from the clear space (3) by means of a second port (8) or expulsion port.

In the configuration shown the ports (7, 8) consist of internally hollow essentially cylindrical bodies defining a respective passage that puts in communication the sealed clear space (3) or third chamber of the body (1) with the outside. The cylindrical body that constitutes the ports (7, 8) is preferably made in such a way as to be particularly short, above all with respect to the solutions commonly employed in the prior art. For example the length (L) of the duct of the ports (7, 8) can be between 8 mm and 20 mm, preferably between 10 mm and 15 mm.

In the preferred embodiment of the present invention the one-way valves necessary to adjust the input and output flow from the clear space (3) or third chamber, whose use is known in the prior art, are advantageously positioned in the respective connecting pipes that are connected to the ports (7, 8). The connection of the pipes occurs by means of a connection (23) with which each of the ports (7, 8) is provided in correspondence of a respective end that protrudes outside the body (1).

The body (1) is made of a rigid material compatible for the use inside the human body or a material coated with a coating compatible for the use inside the human body. For example the body (1) can be made of polyethilene terephtalate such as the product commercially known by the name of dacron, or the product commercially known by the name of delrin, or carbon plastic materials such as pyrocarbonate or also metal materials such as special steels, titanium, titanium alloys of the type commonly used in prosthetic medicine, tantalum or any other suitable material.

The covers (16, 16', 16") are made of a rigid material compatible for the use inside the human body or a material coated with a coating compatible for the use inside the human body. For example the covers (16, 16', 16") can be made of polyethylene terephtalate such as the product commercially known by the name of dacron, or the product commercially known by the name of delrin, or carbon plastic materials such as pyrocarbonate or also metal materials such as special steels, titanium, titanium alloys of the type commonly used in prosthetic medicine, tantalum or any other suitable material.

The membranes (17, 17', 17") are made of a flexible material compatible for the use inside the human body and also hemocompatible or a material coated with a coating compatible for the use inside the human body and also hemocompatible. For example the membranes (17, 17', 17") can be made of silicone or elastomeric materials or silicone elastomers such as polysiloxanes among which polydimethylsiloxane, for example in the form of a product commercially known by the name of silastic. In general the membranes (17, 17', 17") are made of a material having characteristics such as to make the membranes slightly yielding or flexible to perform the pumping function.

During use, a gas or gaseous fluid is sequentially pumped and sucked inside the first chamber (4) and second chamber (5) that are controlled in a synchronous way with respect to each other. The respective chambers are supplied with gas or gaseous fluid alternatively under pressure and depressurization, that is to say, alternatively with positive pressure and negative pressure, so as to alternately draw the membranes reciprocally near and apart to decrease and increase respectively the volume of the clear space performing a pumping action with a blood flow rate depending on the number of times in which the pressure and the depressurization are provided in the time unit, that is to say, in which the positive pressure and the negative pressure are provided in the time unit.

The first chamber (4) and the second chamber (5) being delimited (FIG. 5) on one side by a rigid wall made up of the covers (16, 16', 16") and on the other side by the flexible membranes (17, 17', 17"), following the pumping and suction action of the gas or gaseous fluid within the chambers (4, 5) themselves, act as two reverse lungs that, inflating, are used to compress in a pulsating way the clear space (3) or third chamber providing the pulsating pumping action by means of the deflection of the respective opposite membranes (17, 17', 17"). The suction and pumping action performed on the clear space (3) or third chamber is translated (FIG. 4) into a blood flow that:

is sucked into the clear space (3) or third chamber by means of the first port (7) through an external check valve oriented in such a way as to enable only the flow directed towards the clear space (3) or third chamber;

is pumped out of the clear space (3) or third chamber by means of the second port (8) through an external check valve oriented in such a way as to enable only the flow directed out of the clear space (3) or third chamber.

Externally the device for cardiocirculatory assistance (19) has a shape with a body (1) essentially (FIG. 1) circular in section having a limited width with outwardly projecting sidewalls (FIG. 2) in correspondence of the first and second chamber. In the lower apical zone there is a connection (6) for a pipe of connection to the pneumatic energy source that is used to supply the two opposite chambers (4, 5). On the opposite side of said pneumatic connection (6) there are (FIG. 4) the two ports (7, 8) for pumping the blood having a circular cross-section of a suitable diameter. Furthermore, the body (1) has a shape that, according to a side view (FIG. 2, FIG. 5) is tapered from the top downwards, that is to say, it has a shape in which a first width (S1) of the clear space (3) or third chamber in the zone of the body (1) situated near the ports (7, 8) is greater than a second width (S2) of the clear space (3) or third chamber in the zone of the body (1) situated near the connection (6). For example the first width (S1) in the zone of the body (1) situated near the ports (7, 8) can be between 22 and 28 mm, preferably of the order of 25 millimetres. For example the second width (S2) of the clear space (3) or third chamber in the zone of the body (1) situated near the connection (6) can be between 12 and 18 mm, preferably of the order of 15 millimetres.

In general the body (1) can have a shape that, according to a side view (FIG. 2, FIG. 5) is tapered from the top downwards, that is to say, it has a shape in which a first width (S1) of the clear space (3) or third chamber in the zone of the body (1) situated near the ports (7, 8) is greater than a second width (S2) of the clear space (3) or third chamber in the zone of the body (1) situated near the connection (6). For example it can be provided that the body has an average width between 16 and 23 mm, preferably an average width of about 20 mm.

The first port (7), namely that of input of the blood flow within the clear space (3) or third chamber, has a first diameter (D1). The second port (8), namely that of output of the blood flow from the clear space (3) or third chamber, has a second diameter (D2). The first diameter (D1) is greater than or equal to the second diameter (D2). For example the first diameter (D1) can be between 18 and 20 mm. For example the second diameter (D2) can be between 15 and 17 mm. The thickness of the wall of the duct made up of the first port (7) or of the second port (8) can be for example between 1 and 2 mm.

Advantageously, in the preferred embodiment of the present invention, the first diameter (D1) is greater than the second diameter (D2), this shape favouring the desired establishment of the laminar blood flow in combination with the further characteristics of countersinking of the perimetrical surface (2) and angle of the axes of the ports (7, 8). In fact, the blood pressure in correspondence of the first port (7) is lower than the blood pressure in correspondence of the second port (8) and, as consequence, the fact of providing a first port (7) having a diameter greater than the diameter of the second port (8) allows to obtain an as low as possible resistance to the blood flow entering the device in correspondence of the lowest pressure input point, that is to say, in correspondence of the first port (7).

Thus, it should be understood that, by pressing the clear space (3) or third chamber, the blood comes out of the second port (8) it being prevented from flowing back through the first port (7) due to the presence of the respective first external one-way valve. When, on the other hand, the membrane (17, 17', 17") goes back to the rest position due to the elastic return of the flexible material of which it is made or under the suction action of the pneumatic system, then the phase of suction of the blood through the first port (7) takes place, the suction from the second port (8) being prevented by the presence of the respective second external one-way valve. In this way one obtains a sucking-pressing pump, without mechanical parts and parts subject to wear. The ports (7, 8) are constructed in such a way as to be easily engaged with hemocompatible flexible tubes, commonly used in heart surgery techniques, such as hemocompatible flexible tubes of hemocompatible polyamide resin. The fixing of the hemocompatible flexible tubes can occur, for example, by means of an annular connection (23) present on the perimetrically external edge of the ports (7, 8).

A first flexible tube engaged on the first port (7) is used to take the blood from an atrium, for example by means of an atrioventricular cannula, or from other zones of the cardiovascular apparatus. A second tube engaged on the second port (8) is used to return the blood under pressure to the blood vessels of the systemic circle or the pulmonary circle, according to the type of ventricular assist chosen.

The clear space (3) or third chamber of the body (1), in which the circulation of the blood takes place, is separate from the peripheral zone, consisting of the first chamber (4) and second chamber (5), by means of the membranes (17, 17', 17"). The first chamber (4) and the second chamber (5), constituting the elastic and/or flexible opposite chambers, can be of different nature and shape, and transmit to the blood the necessary pressure energy. The peripheral zone is closed by means of covers (16, 16', 16"). The first chamber (4) and the second chamber (5), constituting the elastic and/or flexible opposite chambers, under the action of the increase in pressure due to the introduction of gas or gaseous fluid, inflate and vice versa, therefore in association with the respective one-way valves to the blood ducts one obtains pumping by means of the induced change in the volume of the clear space (3) or third chamber.

In conclusion, it is a closed pump of the type with opposite membranes whose pulse is induced by compressed gas or gaseous fluid, for example oxygen or air or inert gases in general, pumped from the outside through a thin cannula passing within the user's body from the outside and transmits the pressure pulses from a respective external electric pump applied outside the human body and therefore easily controllable and adjustable. In this way inside the body there is no electrical apparatus. The blood flow that is obtained is of pulsatile nature. Therefore, the pneumatic energy is characterised by pressure and depressurization waves, that is to say, alternatively with positive pressure and negative pressure, obtained by means of an external pump, necessary for the reciprocating motion of the opposite flexible elastic chambers. The external pump can be an electro-pneumatic operating unit, powered by a battery and/or by accumulators. Obviously the external pump can be of any type, such as with a piston or with a membrane actuated by a cam.

Therefore, the device for cardiocirculatory assistance (19) comprises a substantially rigid central body (1) provided with an internal clear space (3) open on the two opposite sides and having an essentially circular shape. The clear space (3) is laterally closed by a pair of membranes (17, 17', 17") that can flex for the pumping of blood, whose internal geometry is shaped hydrodynamically in such a way as to avoid blood stagnation zones that may result in the formation of thrombi.

In fact, the particular shape of the clear space (3) or third chamber has been conceived in such a way as to limit or, at most, cancel the occurrence of blood stagnations.

In particular the desired effect is obtained by means of the following characteristics, preferably in combination with one another:
a) essentially circular shape of the clear space (3) or third chamber, which will have an internal diameter between 40 and 60 mm, preferably between 45 and 55 mm, the preferred value being essentially of about 50 millimetres;
b) first angle (A) between the axis (9) of the first port (7) and the axis (10) of the second port (8) between (FIG. 1) 18 degrees and 27 degrees, preferably between 20 and 25 degrees, the preferred value being essentially of about 23 degrees;
c) distance (Z) between the reciprocally close edges of the first port (7) and second port (8) between (FIG. 1) 15 and 20 millimetres, the preferred value being essentially of about 18 millimetres;

Preferably (FIG. 1), by defining a pair of reciprocally orthogonal axes with reference to the essentially circular clear space (3) of the body (1) namely a first axis (11) of the clear space (3) and a second axis (12) of the clear space (3) passing through the centre of the essentially circular shape, the axis (10) of the second port (8) is arranged with respect to the body (1) according to a configuration in which the axis (10) of the second port (8) forms a second angle (B) with a first axis (11) of the essentially circular clear space (3), the second angle (B) being between 30 and 40 degrees, preferably between 32 and 37 degrees, even more preferably the second angle (B) between the axis (10) of the second port (8) and the first axis (11) of the clear space (3) being of about 35 degrees.

The distance between:
the point of intersection between the axis (9) of the first port (7) and the axis (10) of the second port (8); and
the point of intersection between the first axis (11) of the clear space (3) and the second axis (12) of the clear space (3);
is between 9 and 15 mm, preferably it is of about 12 mm.

Furthermore the clear space (3) or third chamber has (FIG. 5) a shape with a countersunk surface in correspondence of the internal perimetrical surface (2) of the clear space (3) or third chamber, the countersunk surface contributing to the establishment of the desired laminar flow along with the further characteristics of the device such as the angle between the ports (7, 8) and the greater diameter of the first port (7) with respect to the diameter of the second port (8).

In particular, the clear space (3) or third chamber has a shape with a countersunk surface in correspondence of an internal perimetrical surface (2) of the clear space (3) or third chamber, the countersunk surface constituting a progressive increase in the volume of the clear space according to an increase direction symmetrically oriented from the first side (21) and second side (22) of the body (1) towards the centre of the internal perimetrical surface (2) of the clear space (3) or third chamber.

Particularly important is also the ratio between the diameter of the clear space (3) or third chamber and the average width of the previously described tapered shape of the body (1) in which the average width is between 16 and 23 mm, preferably the average width being of about 20 mm.

For example the device (1) can be characterised by a ratio between the diameter of the clear space (3) or third chamber and the average width of the clear space (3) or third chamber between 2.3 and 2.7, preferably of approximately 2.5.

In this way one can provide an embodiment suitable for an adult having a diameter of the clear space (3) or third chamber of 50 mm and an average width of the tapered shape of the body (1) of 20 mm, with a ratio between the diameter and the average width of 2.5.

One can provide an embodiment suitable for paediatric use having a diameter of the clear space (3) or third chamber of 40 mm and an average width of the tapered shape of the body (1) of 17 mm, with a ratio between the diameter and the average width of 2.35.

One can provide an embodiment suitable for an adult having a diameter of the clear space (3) or third chamber of 60 mm and an average width of the tapered shape of the body (1) of 23 mm, with a ratio between the diameter and the average width of 2.6.

Advantageously, thanks to size reduction, paediatric use is also possible, there being the possibility to reduce the sizes of the device with size ratios relative to the various elements, as previously illustrated by the size examples.

In particular, with reference to the following table, therefore, one can provide embodiments for use in adults and embodiments for paediatric use characterised, in general, by a size scaling of the clear space according to a scaling ratio such as to maintain the ratio between the diameter and the average width of the clear space in a range between 2.3 and 2.7.

TABLE 1

| | Device suitable for: | |
|---|---|---|
| | use in adults | paediatric use |
| Internal diameter of clear space (3) | between 50 and 60 mm | between 40 and 50 mm |
| Average width of clear space (3) | between 20 and 24 mm | between 16 and 20 mm |
| Diameter/ average width ratio | about 2.5 | about 2.5 |

The stated values are not the result of an arbitrary choice, but they are the result of studies and experiments that allowed to obtain optimal configuration values such as to extremely facilitate the establishment of a laminar blood flow inside the clear space (3) or third chamber, while considerably reducing the potential blood stagnation zones, such as the zone enclosed by the clear space (3) or third chamber in correspondence of the portion between the first port (7) and second port (8). With reference to said portion, the use of the particular angulation between the axis (9) of the first port (7) and the axis (10) of the second port (8) according to the previously defined first angle (A), in combination with the proximity between the ports (7, 8) obtained by means of the reduced distance (Z) between the reciprocally close edges of the first port (7) and second port (8), advantageously allows both to reduce the risk of occurrence of blood stagnations and to obtain the establishment of a laminar blood flow within the clear space (3) or third chamber and allowing a reduction in the cellular trauma to which the blood is subjected.

Furthermore, the risk of potential stagnations is also reduced by the internal washing action of the clear space (3) or third chamber performed by means of a rotary blood flow, obtained both by virtue of the essentially circular shape of the clear space (3) or third chamber, but also thanks to the particular angulation between the axis (9) of the first port (7) and the axis (10) of the second port (8) according to the previously defined first angle (A).

The external electro-pneumatic operating unit, availing itself of electromechanical devices of the prior art, is compact and lightweight so as to be able to be carried easily by the carrier of the device, in a small bag, or hooked to a belt. The above-mentioned operating unit can have adjusting devices, both manual and automatic, such as to enable a wide variation in the flow emitted by the assistance device and pressure monitoring devices such as pressure sensors. The pulse frequency imposed to the device can be indicatively between 50 and 200 beats per minute and can be varied, both manually and automatically, by means of adjusting systems present in the electro-pneumatic operating unit itself. Thus, it can be inferred that the average flow rate emitted by the device is strictly dependent on the frequency of the asynchronous pulses. As to the lack of synchronism between the natural heart beats and those of the assistance device, it has been found, both experimentally and clinically, that the ventricular assistance method, by means of high-frequency asynchronous pulses, is not in contrast with the principles of a correct blood perfusion and that this method does not negatively affect the behaviour of the assisted natural ventricle. Moreover, it has been found that, based on the use of low range devices, the desired average flow rate values are reached equally by increasing the frequency. Only following this strategy and making the inside of the assistance device without driving members, as in this case, it is possible to realize elements that, due to their small size and low weight, are really implantable inside the chest. Such statements are confirmed by the fact that at present ventricular assistance devices exist and have been experimented based on the principle of centrifugal pumps, therefore they are able to provide only a flow of the continuous type and thus completely out of any possible synchronization with the heartbeat. While by the method of continuous artificial perfusion there is no possibility of synchronism between the systolic diastolic phases of the assisted heart, with respect to those of the assistance device, in the case of the high frequency asynchronous pulses the physical phenomenon of the beats between the frequency of the assisted heart, with respect to the frequency of the assistance ventricle, takes place. That is to say, the ventricle of the assisted heart is also periodically in a correct phase relationship with the assistance device and, only in this situation, can display its natural reduced pressure range.

However, the solution according to the invention can be used both in a synchronized and a non-synchronized pulsatile way depending on the structural and physiological nature of the user.

Obviously the execution details can change in any case and be built of polymeric material or with substances of other nature made hemocompatible by means of a coating. Said details can be combined with one another by means of screws, welding, gluing or other methods.

The suction and delivery one-way valves, characterized by spontaneous opening, are those used in the surgical implants of valve replacement, but, however, it is possible to use specially manufactured valves of other nature. Advantageously it is provided that the one-way valves are housed outside with respect to the ports (7, 8) of the device (19), that is to say, it is provided that the one-way valves are inserted into the flexible tubes connected to said ports (7, 8). In this way there is obviously greater operating safety and greater ease of intervention. Therefore, the device (19) in this embodiment is without one-way valves.

Equally advantageously, the central body (1), whose internal cavity is affected by the blood flow, can be made in such a way that the clear space (3) or third chamber has a geometry with a section decreasing towards the opposite bottom with respect to the zone of application of the ports (7, 8), this solution allowing the blood to flow without meeting stagnation zones and to be pushed without traumas also in the furthest zones with respect to input and output ports (7, 8). These characteristics allow to avoid, as much as possible, both thrombogenesis and hemolysis problems.

Equally advantageously, the pneumatic connection between the operating unit and the connection (6) for the pumping gas or gaseous fluid occurs by means of a flexible tube that has a small diameter and is made of flexible plastic material and is provided with a suitable aseptic transcutaneous passage. The electro-pneumatic operating unit produces a pulsatile flow of gas or gaseous fluid whose frequency can be varied both manually and automatically. Said electro-pneumatic operating unit is powered by an electrical accumulator that can also be housed inside the unit itself. The potential danger of leakage of gas or gaseous fluid, as a propulsion means inside the body, is avoided by the current techniques that ensure gas tightness. In fact, the flexible gas duct can be made in one piece with the respective elastic expansion chamber, for example with silicone elastomeric materials (silicone rubber) that ensure perfect and safe compatibility with the human body.

Advantageously, the opposite elastic membranes (17, 17', 17"), that overlook the clear space (3) or third chamber, substantially act as two reverse operating lungs, so as to exert a symmetrical push on the blood. From this characteristic it results that the assistance device is free from mechanical oscillations or vibrations caused by inertial forces or imbalances that can come from the internal dynamics of the device. The mobile parts are subjected to a uniformly distributed mechanical stress, which ensures a long duration. The pulse device is advantageously asynchronous with the natural heart, to be at delivery with fixed pulse and being able to work at a variable frequency in order to obtain a wide variation in the average flow rate. Advantageously the external pumping device can be completed in the preferred embodiment with a very simple small emergency manual pump of the type with a flexible bulb, with exclusion valve. In this case, in case of failure of the external pump, it will be sufficient to open the valve of the bulb and pump manually. A circulatory effect on the blood will thus be surely ensured in that case during emergency.

Advantageously (FIG. 6) it is provided that the elastic membranes (17, 17', 17") are fixed to the device for cardiocirculatory assistance (19) by means of pressing between a respective side (21, 22) of the body (1) and a corresponding coupling edge of the respective cover (16, 16', 16").

In particular the first membrane (17') will be fixed by means of perimetrical pressing of its edge between a first side (21) of the body (1) and a corresponding coupling edge of the first cover (16').

In particular the second membrane (17") will be fixed by means of perimetrical pressing of its edge between a second side (22) of the body (1) and a corresponding coupling edge of the second cover (16").

For both membranes, in correspondence of the coupling portion between the side (21, 22) of the body and the coupling edge of the cover (16, 16', 16") there is a locking and perimetrically sealing zone which consists of a recessed annular seat (13) adapted to house on its inside a corresponding protrusion (18) according to a configuration in which (FIG. 6) the corresponding membrane (17) is pressed within the seat (13) and locked in this position by the protrusion (18) that penetrates the seat (13) creating a perimetrically sealing zone of the chambers (4, 5) for the gas or gaseous fluid. Therefore, the membrane (17) is interposed between the seat (13) and the protrusion (18) when the protrusion (18) is made to penetrate the seat (13) for example under the pushing action exerted by the screws within the holes (14), said screws fixing the cover (16) on the body (1).

The quality of the material that is in contact with the blood, such as the walls of the membranes oriented towards the clear space (3) or the internal walls of the clear space (3) itself, is very important. Such zones must be smooth, that is to say, microscopically endothelium-like.

Moreover, one avoids edges of the internal structure in contact with the blood, creating inlet countersunk surfaces in correspondence of the ports (7, 8) and tapered edges for example in correspondence of the zones of coupling between the sides (21, 22) of the body (1) and the membranes (17, 17', 17").

The device is simplified and constructed with lightweight, resistant material that is notoriously tolerated by the human anatomical tissues including blood. The prosthesis, besides being extremely lightweight and small-sized, is also easy to be produced in its component elements, easy to be composed, easy to be surgically applied. Furthermore, the long-term maintenance for the frequent cardiac pathological chronicity is also facilitated, thus resulting cost-efficient as well.

In general, the present invention relates to (FIG. 1, FIG. 2, FIG. 5) a device for cardiocirculatory assistance (19) constituting a pump for a blood flow in which the device for cardiocirculatory assistance (19) is provided with:

a body (1) made of a body material which is a rigid material wherein the body (1) is provided with an essentially circular clear space (3) delimited by a first side (21) and by a second side (22) of the body (1), the first side (21) and the second side (22) being open in such a way that the clear space (3) constitutes a through-hole in the body (1) between the first side (21) and the second side (22), the body (1) comprising a first port (7) or intake port of the blood flow within the clear space (3) and a second port (8) or expulsion port of the blood flow from the clear space (3);

a pair of covers (16', 16") of which a first cover (16') and a second cover (16") made of a cover material which is a rigid material;

a pair of membranes (17', 17") of which a first membrane (17') and a second membrane (17") made of a membrane material which is a flexible material.

In particular, the first membrane (17') is placed between the first side (21) of the body (1) and the first cover (16') in such a way as to perimetrically seal a first chamber (4) arranged in the first cover (16'), the second membrane (17") is placed between the second side (22) of the body (1) and the second cover (16") in such a way as to perimetrically seal a second chamber (5) arranged in the second cover (16"), the second side (22) of the body (1) being the opposite side of the body (1) with respect to the first side (21). In practice, the first membrane (17') and the second membrane (17") further seal the clear space (3) of the body (1) thus constituting a third chamber.

The device for cardiocirculatory assistance (19) is provided with a circuit (6, 15) for the passage of a gas or gaseous fluid and the first chamber (4) and the second chamber (5) are intended to be supplied with the gas or gaseous fluid alternatively under pressure and depressurization, that is to say, alternatively with positive pressure and negative pressure so that a reciprocating pumping motion of the membranes (17', 17") is established so as to alternately draw the membranes reciprocally near and apart. The first port (7) or intake port and the second port (8) or expulsion port are arranged in such a way that the blood flow moves from the first blood intake port (7) towards the second blood expulsion port (8) following an essentially circular path within the clear space (3) or third chamber.

The first port (7) or intake port and the second port (8) or expulsion port are arranged on the body (1) in such a way that the axis (9) of the first port (7) or intake port and the axis (10) of the second port (8) or expulsion port form a first angle (A) between 18 degrees and 27 degrees, facilitating the establishment of a laminar motion of said blood flow within the clear space (3) or third chamber.

Preferably the axis (10) of the second port (8) is arranged with respect to the body (1) according to a configuration in which the axis (10) of the second port (8) forms a second angle (B) with a first axis (11) of the essentially circular clear space (3), the second angle (B) being between 30 and 40 degrees, preferably between 32 and 37 degrees, even more preferably the second angle (B) between the axis (10) of the second port (8) and the first axis (11) of the clear space (3) being of about 35 degrees.

The first port (7) and the second port (8) are arranged on said body (1) according to a configuration in which the internal edges of the passages made up of the first port (7) and second port (8) are arranged at a distance (Z) between 15 and 20 millimetres, the preferred value being essentially of about 18 millimetres.

Each of the membranes (17', 17") is interposed between the respective side (21, 22) of the body (1) and the respective cover (16', 16") according to a configuration in which the membrane is pressed between the body (1) and one edge of the cover (16', 16"), in correspondence of a coupling portion between the body (1) and the edge of the cover (16, 16', 16") there being a locking and perimetrically sealing zone which consists of a recessed annular seat (13) adapted to house on its inside a corresponding protrusion (18) according to a configuration in which the corresponding membrane (17', 17") is pressed within the seat (13) and locked in this position by the protrusion (18) penetrating the seat (13) and creating a perimetrically sealing zone of the chambers (4, 5).

The circuit (6, 15) for the passage of the gas or gaseous fluid includes a connection (6) arranged on the body (1) which is in flow communication with a duct for the passage of the gas or gaseous fluid (15) obtained within the body (1), the duct for the passage of the gas or gaseous fluid (15) being in its turn in flow communication with corresponding extensions of the duct itself that are obtained within the body of the covers (16', 16") according to a configuration in which the extensions of the duct put in flow communication the duct for the passage of the gas or gaseous fluid (15) with the respective first chamber (4) and second chamber (5).

The body (1) has a tapered shape according to a tapering direction oriented as moving away with respect to a portion of the body (1) in which there are the first port (7) or intake port and the second port (8) or expulsion port, the clear space (3) or third chamber of the body (1) having a shape in which a first width (S1) of the clear space (3) or third chamber in the zone of the body (1) situated near the ports (7, 8) is greater than a second width (S2) of the clear space (3) or third chamber in the zone of the body (1) situated in correspondence of an opposite portion of the body (1) with respect to the portion of the body (1) in which there are the first port (7) or intake port and the second port (8) or expulsion port.

The ratio between the diameter of the essentially circular clear space (3) or third chamber and an average width of the clear space (3) or third chamber along the tapering direction is between 2.3 and 2.7, preferably the ratio being approximately of 2.5.

Finally, the present invention also relates to an apparatus for cardiocirculatory assistance comprising an electro-pneumatic operating unit intended to supply a gas or gaseous fluid alternatively under pressure and depressurization, that is to say, alternatively with positive pressure and negative pressure, wherein the operating unit is connected by means of respective connecting pipes to a pump for a blood flow wherein the pump for the blood flow is made in the form of a device for cardiocirculatory assistance (19) according to what has been previously described.

The description of the present invention has been made with reference to the enclosed figures in a preferred embodiment, but it is evident that many possible changes, modifications and variations will be immediately clear to those skilled in the art in the light of the previous description. Thus, it must be underlined that the invention is not limited to the previous description, but it includes all the changes, modifications and variations in accordance with the appended claims.

The invention claimed is:

1. A device for cardiocirculatory assistance constituting a pump for a blood flow comprising:
   a body made of a body material which is a rigid material wherein the body is provided with an essentially circular clear space delimited by a first side and by a second side of the body, the first side and the second side being open in such a way that the clear space constitutes a through-hole in the body between the first side and the second side, the body comprising a first port for intake of blood flow within the clear space and a second port for expulsion of the blood flow from the clear space;
   a pair of covers of which a first cover and a second cover made of a cover material which is a rigid material;
   a pair of membranes of which a first membrane and a second membrane made of a membrane material which is a flexible material;
   wherein
   the first membrane is placed between the first side of the body and the first cover in such a way as to perimetrically seal a first chamber arranged in the first cover;
   the second membrane is placed between the second side of the body and the second cover in such a way as to perimetrically seal a second chamber arranged in the second cover, the second side of the body being the opposite side of the body with respect to the first side;
   the first membrane and the second membrane further sealing the clear space of the body in such a way as to form a third chamber;
   the device for cardiocirculatory assistance being provided with a circuit for the passage of a gas or gaseous fluid, the first chamber and the second chamber being configured to be supplied with the gas or gaseous fluid alternatively with positive pressure and negative pressure so that a reciprocating pumping motion of the membranes is established so as to alternately draw the membranes reciprocally near and apart, wherein the first port and the second port are placed in such a way that the blood flow moves from the first port towards the second port along an essentially circular path within the clear space, the clear space being the third chamber;
   wherein
   the first port and the second port port are arranged on the body in such a way that an axis of the first port and an axis of the second port form a first angle between 18 degrees and 27 degrees, facilitating the establishment of a laminar motion of said blood flow within the clear space.

2. The device for cardiocirculatory assistance constituting a pump for a blood flow according to claim 1 wherein
the first angle between the axis of the first port and the axis of the second port is between 20 and 25 degrees.

3. The device for cardiocirculatory assistance constituting a pump for a blood flow according to claim 1, wherein
the axis of the second port is arranged with respect to the body according to a configuration in which the axis of the second port forms a second angle with a first axis of the essentially circular clear space, the second angle being between 30 and 40 degrees.

4. The device for cardiocirculatory assistance constituting a pump for a blood flow according to claim 3, wherein
the second angle between the axis of the second port and the first axis of the clear space is between 32 and 37 degrees.

5. The device for cardiocirculatory assistance constituting a pump for a blood flow according to claim 1, wherein
the first port and the second port are arranged on said body according to a configuration in which the internal edges of the passages made up of the first port and second port are arranged at a distance between 15 and 20 millimetres.

6. The device for cardiocirculatory assistance constituting a pump for a blood flow according to claim 1, wherein
each of the membranes is interposed between the respective side of the body and the respective cover according to a configuration in which the membrane is pressed between the body and one edge of the cover, in correspondence of a coupling portion between the body and the edge of the cover there being a locking and perimetrically sealing zone which consists of a recessed annular seat adapted to house on its inside a corresponding protrusion according to a configuration in which the corresponding membrane is pressed within the seat and locked in this position by the protrusion penetrating the seat and creating a perimetrically sealing zone of the chambers.

7. The device for cardiocirculatory assistance constituting a pump for a blood flow according to claim 1, wherein
the circuit for the passage of the gas or gaseous fluid includes a connection arranged on the body which is in flow communication with a duct for the passage of the gas or gaseous fluid obtained within the body, the duct for the passage of the gas or gaseous fluid being in its turn in flow communication with corresponding extensions of the duct itself that are obtained within the body of the covers according to a configuration in which the extensions of the duct put in flow communication the duct for the passage of the gas or gaseous fluid with the respective first chamber and second chamber.

8. The device for cardiocirculatory assistance constituting a pump for a blood flow according to claim 1, wherein
the body has a tapered shape according to a tapering direction oriented as moving away with respect to a portion of the body in which there are the first port or intake port and the second port or expulsion port, the clear space or third chamber of the body having a shape in which a first width of the clear space or third chamber in the zone of the body situated near the ports is greater than a second width of the clear space or third chamber in the zone of the body situated in correspondence of an opposite portion of the body with respect to the portion of the body in which there are the first port or intake port and the second port or expulsion port.

9. The device for cardiocirculatory assistance constituting a pump for a blood flow according to claim 8, wherein
the ratio between the diameter of the essentially circular clear space or third chamber and an average width of the clear space or third chamber along the tapering direction is between 2.3 and 2.7.

10. The device for cardiocirculatory assistance constituting a pump for a blood flow according to claim 9, wherein
an average width of the clear space or third chamber along the tapering direction is between 16 and 23 mm.

11. The device for cardiocirculatory assistance constituting a pump for a blood flow, according to claim 10, wherein
a first width of the clear space in a zone of the body situated near the first and second ports is between 22 and 28 mm;
a second width of the clear space in a zone of the body is situated in correspondence of an opposite portion of the body with respect to the portion of the body in which there are the first port and the second port is between 12 and 18 mm.

12. The device for cardiocirculatory assistance constituting a pump for a blood flow, according to claim 9, wherein
the clear space having an essentially circular shape has an internal diameter between 40 and 60 millimetres.

13. The device for cardiocirculatory assistance constituting a pump for a blood flow, according to claim 9, wherein
it is a device for cardiocirculatory assistance for paediatric use in which the average width of the clear space along a tapering direction is between 16 and 20 millimetres.

14. The device for cardiocirculatory assistance constituting a pump for a blood flow, according to claim 9, wherein
it is a device for cardiocirculatory assistance for paediatric use in which the clear space having an essentially circular shape has an internal diameter between 40 and 50 millimetres.

15. The device for cardiocirculatory assistance constituting a pump for a blood flow, according to claim 1, wherein
the first intake port has a first diameter which is greater than a second diameter which is the diameter of the second port.

16. The device for cardiocirculatory assistance constituting a pump for a blood flow according to claim 15, wherein
the first diameter is between 18 and 20 mm and the second diameter is between 15 and 17 mm.

17. The device for cardiocirculatory assistance constituting a pump for a blood flow, according to claim 1, wherein
the clear space has a shape with a countersunk surface in correspondence of an internal perimetrical surface of the clear space, the countersunk surface constituting a progressive increase in the volume of the clear space according to an increase direction symmetrically oriented from the first side and second side of the body towards the centre of the internal perimetrical surface of the clear space.

18. The device for cardiocirculatory assistance constituting a pump for a blood flow, according to claim 1, wherein
the material of the body is selected from the group consisting of polyethylene terephthalate, a product commercially known by the name of dacron, a product commercially known by the name of delrin, carbon plastic materials, pyrocarbonate, metal materials.

19. The device for cardiocirculatory assistance constituting a pump for a blood flow, according to claim 1, wherein the material of the cover is selected from the group consisting of polyethylene terephthalate, a product commercially known by the name of dacron, a product commercially known by the name of delrin, carbon plastic materials, pyrocarbonate, metal materials.

20. The device for cardiocirculatory assistance constituting a pump for a blood flow, according to claim 1, wherein
the material of the membrane is selected from the group consisting of elastomeric or silicone materials or silicone elastomers, polysiloxanes, polydimethylsiloxane, a product commercially known by the name of silastic.

21. An apparatus for cardiocirculatory assistance comprising an electro-pneumatic operating unit intended to supply a gas or gaseous fluid alternatively with positive pressure and negative pressure wherein the operating unit is connected by means of respective connecting pipes to a pump for a blood flow, wherein
the pump for the blood flow is made in the form of a device for cardiocirculatory assistance according to claim 1.

* * * * *